(12) United States Patent
Comaniciu et al.

(10) Patent No.: US 10,610,302 B2
(45) Date of Patent: Apr. 7, 2020

(54) LIVER DISEASE ASSESSMENT IN MEDICAL IMAGING

(71) Applicant: Siemens Healthcare GmbH, Erlangen (DE)

(72) Inventors: Dorin Comaniciu, Princeton Junction, NJ (US); Thomas Pheiffer, Langhorne, PA (US); David Liu, Richardson, TX (US); Ankur Kapoor, Plainsboro, NJ (US); Tommaso Mansi, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 455 days.

(21) Appl. No.: 15/641,514

(22) Filed: Jul. 5, 2017

(65) Prior Publication Data

US 2018/0078313 A1     Mar. 22, 2018

Related U.S. Application Data

(60) Provisional application No. 62/396,842, filed on Sep. 20, 2016.

(51) Int. Cl.
*A61B 34/10* (2016.01)
*G06F 19/00* (2018.01)
(Continued)

(52) U.S. Cl.
CPC ............ *A61B 34/10* (2016.02); *A61B 5/0035* (2013.01); *A61B 5/055* (2013.01); *A61B 5/4244* (2013.01);
(Continued)

(58) Field of Classification Search
CPC ......... A61B 34/10; A61B 18/02; A61B 18/12; A61B 5/0035; A61B 8/485; A61B 5/4244; A61B 5/055; A61B 18/00; A61B 5/0263; A61B 2018/00529; A61B 8/5223; A61B 2034/105; A61B 2034/104;
(Continued)

(56) References Cited

U.S. PATENT DOCUMENTS

| | | | |
|---|---|---|---|
| 2011/0245660 A1* | 10/2011 | Miyamoto | A61B 6/032 600/424 |
| 2013/0108127 A1* | 5/2013 | Boettger | G06F 19/321 382/131 |

(Continued)

OTHER PUBLICATIONS

Audigier, Chloé, et al. "Efficient lattice Boltzmann solver for patient-specific radiofrequency ablation of hepatic tumors." IEEE Transactions on Medical Imaging 34.7 (2015): 1576-1589.

*Primary Examiner* — Sanjay Cattungal

(57) ABSTRACT

For liver modeling from medical scan data, multiple modalities of imaging are used. By using multiple modalities of imaging in combination with generative modeling, a more comprehensive and informed assessment may be performed. The generative modeling may allow feedback of effects of proposed therapy on function of the liver. This feedback is used to update the liver function information based on the imaging. Based on the computerized modeling with information from various imaging modes, an output based on more comprehensive information and patient personalized modeling and feedback may be provided to assist the physician.

13 Claims, 3 Drawing Sheets

(51) Int. Cl.
*G06T 11/00* (2006.01)
*A61B 18/00* (2006.01)
*A61B 5/055* (2006.01)
*A61B 5/00* (2006.01)
*A61B 8/08* (2006.01)
*G16H 50/30* (2018.01)
*G16H 50/50* (2018.01)
*A61B 18/12* (2006.01)
*A61B 18/02* (2006.01)
*A61N 7/00* (2006.01)
*G06T 7/00* (2017.01)
*G16H 30/40* (2018.01)
*G16H 40/63* (2018.01)
*G06K 9/62* (2006.01)
*A61B 6/03* (2006.01)
*G06T 7/11* (2017.01)
*A61N 5/10* (2006.01)
*A61B 5/026* (2006.01)

(52) U.S. Cl.
CPC .............. *A61B 8/485* (2013.01); *A61B 18/00* (2013.01); *A61B 18/02* (2013.01); *A61B 18/12* (2013.01); *A61N 7/00* (2013.01); *G06F 19/321* (2013.01); *G06K 9/6289* (2013.01); *G06T 7/0012* (2013.01); *G06T 11/003* (2013.01); *G16H 30/40* (2018.01); *G16H 40/63* (2018.01); *G16H 50/30* (2018.01); *G16H 50/50* (2018.01); *A61B 5/0263* (2013.01); *A61B 6/03* (2013.01); *A61B 8/5223* (2013.01); *A61B 2018/00529* (2013.01); *A61B 2018/00535* (2013.01); *A61B 2018/00577* (2013.01); *A61B 2034/104* (2016.02); *A61B 2034/105* (2016.02); *A61N 5/1002* (2013.01); *A61N 5/103* (2013.01); *G06K 9/6256* (2013.01); *G06K 9/6267* (2013.01); *G06K 2209/051* (2013.01); *G06T 7/11* (2017.01); *G06T 2207/10081* (2013.01); *G06T 2207/10088* (2013.01); *G06T 2207/30024* (2013.01); *G06T 2207/30056* (2013.01); *G06T 2207/30096* (2013.01); *G06T 2210/41* (2013.01)

(58) Field of Classification Search
CPC .......... A61B 2018/00577; A61B 2018/00535; A61B 6/03; G16H 40/63; G16H 30/40; G16H 50/50; G16H 50/30; G06F 19/321; G06K 9/6289; G06K 2209/051; G06K 9/6256; G06K 9/6267; A61N 5/103; A61N 5/1002; A61N 7/00; G06T 7/0012; G06T 11/003; G06T 2210/41; G06T 7/11; G06T 2207/30024; G06T 2207/30056; G06T 2207/30096; G06T 2207/10081; G06T 2207/10088
See application file for complete search history.

(56) References Cited

U.S. PATENT DOCUMENTS

| | | |
|---|---|---|
| 2015/0242588 A1* | 8/2015 | Audigier ................ A61B 34/10 606/41 |
| 2016/0000384 A1 | 1/2016 | Gall et al. |
| 2016/0310107 A1 | 10/2016 | Mansi et al. |

* cited by examiner

LIVER DISEASE ASSESSMENT IN MEDICAL IMAGING

RELATED APPLICATIONS

The present patent document claims the benefit of the filing dates under 35 U.S.C. § 119(e) of Provisional U.S. Patent Application Ser. No. 62/396,842, filed Sep. 20, 2016, which is hereby incorporated by reference.

BACKGROUND

The present embodiments relate to liver disease assessment. Liver disease requires early attention to minimize risks of chronic liver failure and cancer. For instance, primary liver cancer is the second cause of death from cancer and the sixth most common cancer type. In oncology, liver treatment consists of either global strategies (e.g., complete liver transplant), regional strategies (e.g., resection of the diseased part, which is then regenerated naturally), and localized strategies (e.g., arterial embolization, with or without active agents like chemo (TACE) or radioactive elements (TAR), venous embolization, or ablation). While global and regional strategies are the most effective today, localized strategies are minimally-invasive with less side-effects and shorter recovery time. However, the localized strategies often suffer from incomplete treatment and thus recurrence. Today, localized strategies are used if other approaches fail (e.g., as neo-adjuvant for resection) or in combination for maximizing benefit or chance of success of treatment.

As the number of therapeutic option increases, questions arise on what is the best treatment strategy for a given patient in terms of outcome, recovery and side effects. The current liver function in the patient is assessed. A prediction is made for what the liver function will be after intervention. Planning for therapy considers what vessels to target and what vessels to avoid and whether any reactive agent (e.g., chemo pharmaceutical or radiation) will reach the tumor.

Medical imaging may be used for this liver disease assessment. Medical imaging techniques provide powerful tools to visualize the liver and liver function. Physicians must then extrapolate the condition and/or therapy based on the information from the imaging. A limited type or amount of information may be considered. The outcome is predicted based on generalized knowledge from other cases and the current state of the specific patient.

SUMMARY

By way of introduction, the preferred embodiments described below include methods, computer readable media, and systems for liver modeling from medical scan data. By using multiple modes of imaging in combination with generative modeling, a more comprehensive and informed assessment may be performed. The generative modeling may allow feedback of effects of proposed therapy on function of the liver. This feedback is used to update the liver function information based on the imaging. Based on the computerized modeling with information from various imaging modes, an output based on more comprehensive information and patient specific modeling and feedback may be provided to assist the physician.

In a first aspect, a method is provided for liver modeling from medical scan data. An anatomy model of structures of a liver of a patient is generated from scan data of different first and second imaging systems of corresponding different first and second imaging modalities. A substrate model of stiffness of the liver of the patient is generated from scan data of a third imaging modality. A perfusion model of fluid perfusion of the liver of the patient is generated from scan data of a fourth imaging modality. A microvascular model of the liver of the patient is inferred from the anatomy model, substrate model, and perfusion model. A computational model of physiology of the liver is estimated from the substrate model, perfusion model, anatomy model, and the microvascular model. A change in the liver due to therapy is modeled with the computational model. In response to the modeling of the change, the anatomy model, the substrate model, the perfusion model, the microvascular model, or combinations thereof are updated. An image representing function of the liver based on the updated anatomy model, the substrate model, the perfusion model, the microvascular model, or combinations thereof is output.

In a second aspect, a method is provided for liver modeling from medical scan data. An anatomical model of a liver of a patient is generated. A liver function map is estimated from multiple modalities of medical imaging. The liver function map includes substrate properties, perfusion, and microvasculature. A generative liver model is fit to the patient based on the liver function map. The generative liver model includes biomechanics and hemodynamics. A recommendation of a treatment is provided using the generative liver model. Therapy outcome for liver function due to the treatment is calculated with an update of the liver function map. The update provides the therapy outcome. The therapy outcome is output.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
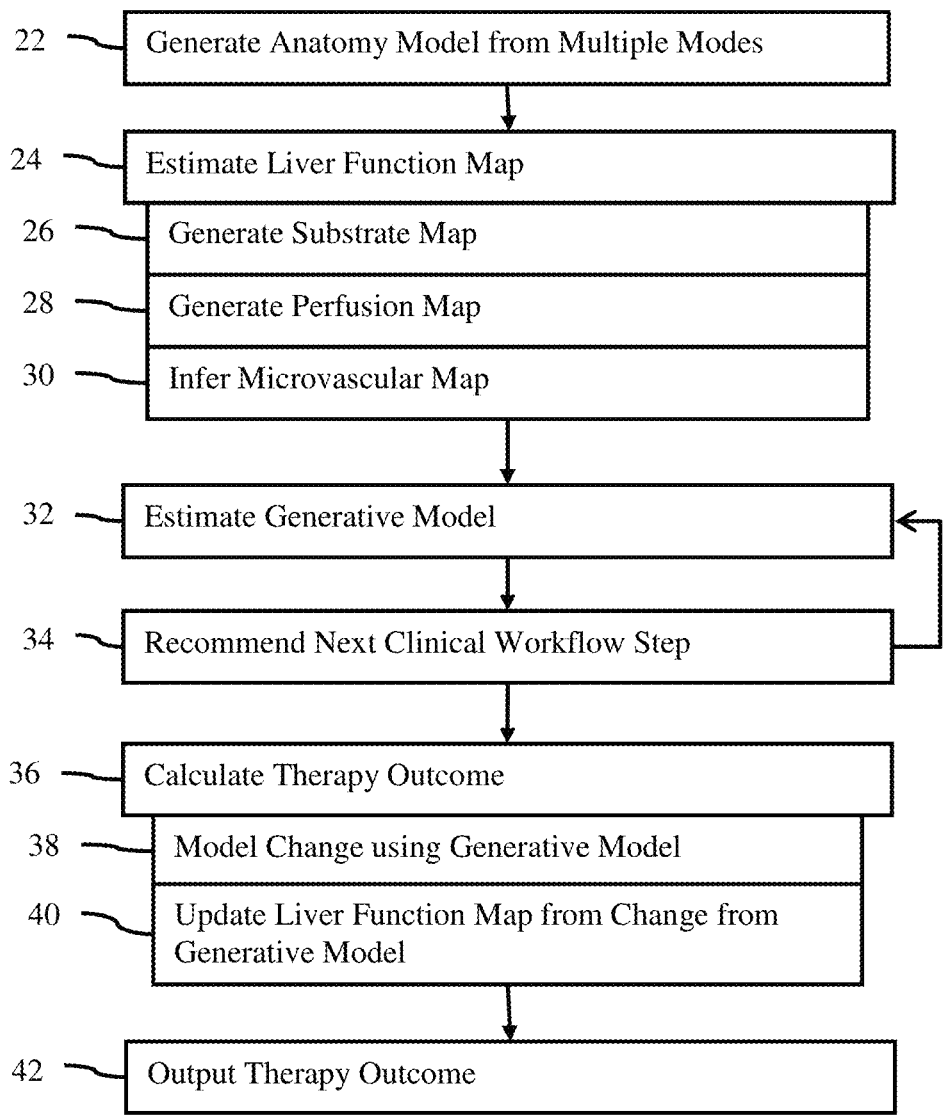
FIG. 1 is a flow chart diagram of one embodiment of a method for liver modeling from medical scan data.

By modeling physiology of a liver of a particular patient, any liver disease of the patient may be better characterized and therapy planned. There is a need for improved image-based tools for liver disease diagnosis, treatment planning, and guidance. The improvement provides more than mere imaging as a source of information to inform physician decisions. Quantitative, reproducible, and integrated assessment of liver function for a patient is provided. Comprehensive liver vascularization understanding (e.g., vascularization is provided from multiple sources, such as liver perfusion, anatomic feeding vessels, and microvasculature)

may be provided for diagnosis, planning, and guidance. Models assess the current liver function and predict the remaining liver function after therapy to maximize the treatment area while preserving as much function as possible, and thus minimize risks of recurrence and side effects.

In one embodiment, a comprehensive, multi-physics liver model is generated from image data for quantitative liver function assessment, therapy selection, planning, and/or guidance. A comprehensive anatomical model of the liver, its vasculature, biliary system and lesions is generated from imaging data. A multi-modality liver function map is estimated by fusing further information with the morphology. Liver tissue substrate and biomechanical properties (e.g., stiffness and/or viscosity) are generated for the liver function map using direct or indirect estimation methods (e.g. inverse modeling). Liver perfusion is quantified for the liver function map. Tumor microvasculature is estimated for the liver function map from the perfusion map, flow images, substrate map, and/or inverse angiogenesis modeling. All this information is combined mathematically to result in one, visual and quantitative map. Then, a generative liver model is built based on the multi-modality liver function map. The generative liver model captures liver perfusion, biomechanics, vessel hemodynamics, and tumor function. From the generative liver model, available lab tests, and known guidelines, a recommendation of a diagnosis or treatment strategy (e.g., transplant, resection, or drug therapy) is provided. Available lab tests and known guidelines may be used directly with the liver function map as well. Therapy outcome indicators (e.g. remaining liver function) are calculated by updating the perfusion map and/or the multi-modality liver function map according to a vessel clamping, a resection, chemo- or radio-embolization, or an ablation strategy, and calculating tissue ablation area given a heat transfer model, device or therapy parameters, and the multi-modality liver function map. In other embodiments, less, additional, or different information is used or combined in the comprehensive, computerized assessment.

Since the modeling is based on different imaging modalities and generative or computational modeling, information useful to the physician may be provided. This second opinion may account for more information and interrelationships of the information than the physician can provide. Feedback based on the generative model to update the liver function information provides model-based or calculated information and imaging representation not performed by physicians.

FIG. 1 shows a method for liver modeling from medical scan data. For comprehensive assessment, information from multiple modalities of medical imaging are used in combination with a physiological model to model changes to the liver and update the functional representation of the liver based on the change.

The method of FIG. 1 is implemented in the order shown (e.g., top to bottom or numerical) or a different order. For example, act 28 may be performed prior to act 26. In another example, act 34 is performed after act 36. The acts may be performed in sequence within minutes or hours of each other. Alternatively, one or more acts are performed in advance of other acts by days or weeks.

Additional, different, or fewer acts may be performed. For example, act 34 is not performed. As another example, one or more sub-acts 26, 28, 30, 38, and/or 40 are not performed. In yet another example, act 42 is not performed.

The method is implemented by a medical diagnostic imaging system, a review station, a workstation, a computer, a picture archiving and communication system (PACS) station, a server, a mobile device, on the cloud, combinations thereof, or other device for image processing medical data. For example, the system or computer readable media shown in FIG. 5 implements the method, but other systems may be used. A hardware processor of any type of system, interacting with memory (e.g., PACS database or cloud storage), user input, display, medical imaging systems, and/or other components, may perform the acts.

The acts may be performed automatically by an image processor. The user causes the patient to be scanned or obtains scan data for the patient from a previous scan. The user may activate the process. Once activated, the anatomy is identified, functional map estimated, generative model estimated, recommendation made, and/or therapy outcome calculated without further user input. User input of locations of the anatomy in any of the scan data may be avoided. Some user input may be provided, such as for changing modeling parameter values, correcting detected locations, indicating therapy and therapy extent to be performed, and/or to confirm accuracy.

The models and/or maps are based on scan data from a patient. This patient-specific modeling may result in representation being different for different patients. For one patient, the model may be different than an average or another patient. Since the modeling relies on the patient-specific scan data, patient specific properties may be determined.

For patient specific modeling, multiple sets of scan data are obtained. Ultrasound, single photon emission computed tomography (SPECT), positron emission tomography (PET), magnetic resonance (MR), angiography, fluoroscopy, x-ray, or computed tomography (CT) data is obtained. Any medical imaging modality capable of scanning a volume including the liver with or without adjacent tissue may be used. Different modalities use different physics to scan, such as CT using x-rays, MR using electrical pulses, and ultrasound using acoustics. Alternatively or additionally, different modalities use different types of sensors or systems. Different modalities may use a same type of scanner, but set to measure different aspects or properties of the patient, such as ultrasound measuring intensity of return, motion or flow, and elasticity as three example modalities with a same type of scanner. By providing scan data from different modalities, different characteristics of the patient's liver are measured.

The scan data sets correspond to data sets interpolated to a regular 3D grid, displayed images, and/or data from any point along the processing chain from sensing to displaying an image. Scan or imaging data may be a frame or volume of data representing a volume. The scan or imaging data may be data from the processing path derived before generating an image or data for a display as an image. A frame or volume of data may be data in an image format or data in a different format (e.g., scan format or representing a three-dimensional grid). The data represents a volume or 3D region of a patient, but scan data representing a projection through the volume in two-dimensions or representing a slice or plane may be used.

The liver volume region includes tissue, fluid, and/or other anatomy structures. Different structures or types of structures react to a given modality of scanning differently. The scan data of different modalities may provide different information about the liver.

In act 22, an anatomical model of the liver of a patient is generated. The liver includes soft tissue, vasculature, and the biliary system. The liver may also include one or more lesions, such as cysts or tumors. The anatomical model represents multiple, such as all, of these anatomical parts of the liver. The anatomy model includes structures of the liver of the patient. The anatomy model is formed from the different structures. For example, meshes, labeling of voxels, or other segmentation are used to represent the different anatomy of the liver.

Structures of the liver are segmented in the most suited modality. The structures are identified from scan data. Different structures may be more accurately detected with different imaging modalities of the same or different imaging systems. For example, MR and CT scans of the liver are performed. The scan data from the MR scan may best reflect or measure liver parenchyma and/or tumors and the scan data from the CT scan may best reflect or measure liver vasculature. The different scan data and corresponding imaging modalities are used to identify different structures. The same structure may be segmented using scan data from different modalities. The results are combined, such as averaged, or both sets of scan data are used to segment.

Different types and/or the same type of segmentation may be used for different structures. Any type of segmentation may be used. Thresholding, region growing, skeletonizing, template matching, filtering, or other imaging processing may be used to determine locations represented by the scan data for the structures. In one embodiment, the segmentation is performed using one or more machine-learnt classifiers. For example, a discriminative probabilistic model detects the locations of anatomy based on probability. The patient specific data is an input feature to the model, such as a machine-learned matrix. The locations associated with the highest probabilities, after any weighting or other consideration, is selected as the location for the anatomy. Different locations have different probabilities for representing the anatomy of interest.

Any machine training may be used. The machine-trained classifier is any one or more classifiers. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perceptron), mixture models, or others. A probabilistic boosting tree may be used. Error-correcting output code (ECOC) may be used. Deep learning or deep reinforcement learning may be used to detect the organ and segment the liver and its structures. Deep adversarial architectures may be used to improve the performance of the segmentation.

The classifier is trained from a training data set using a computer or other machine. Any number of expert annotated sets of data is used. For example, about 200 hundred volumes representing the liver are annotated. The annotation indicates landmarks and/or surfaces within the volumes. The different anatomies of each volume are annotated. This large number of annotations allows learning of relevant features over a large pool of 3-D Haar, steerable features, deep learnt, and/or other features. Each classifier uses the data sets and annotations specific to the anatomy being classified. The classifier learns various feature vectors for distinguishing between a desired anatomy and information not being detected.

Each segmentation includes a mesh or labeled voxels. The anatomy model is formed from the meshes for the different structures. A multi-modality data fusion approach is used. Since the anatomy model is formed from segmentations from different modalities, the coordinate systems of the different modalities are aligned. Images from multiple modalities (e.g. MR, CT) are automatically aligned. Any rigid, affine or non-rigid alignment may be used. For example, a coarse-to-fine image registration is performed to align the coordinate systems. Correlation, minimum sum of absolute differences, and/or landmark matching may be used. Artificial intelligence-based registration may be used, based on deep learning or deep reinforcement learning, to cope with the large image appearance differences, artifacts, or large motion. The alignment is performed prior to segmentation or after segmentation but prior to combination.

The aligned segmentations are fused to form one comprehensive anatomical model. For example, the liver parenchyma (including lobes), vessels (e.g., hepatic arteries, hepatic vein, portal vein, and/or biliary tract), and liver lesions are segmented and the results combined. User input may be provided for editing, confirming, or correcting the segmentation of a particular structure or for the combination of segmentations (e.g., to correct the alignment).

Figure 2:
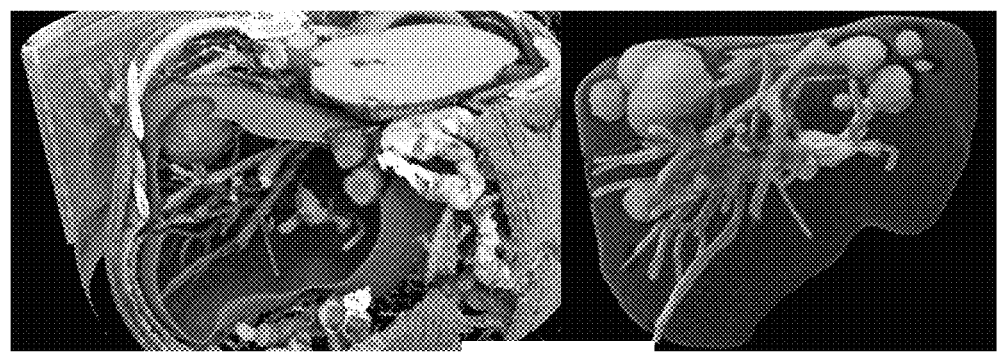
FIG. 2 shows two images of an anatomy model.

FIG. 2 shows two images of examples of anatomy models. The different structures have different brightness or intensity. The images of FIG. 2 are renderings from clipped volumes of the anatomy model for a patient. Different structures are represented in the one model formed by combination of segmentations from different modalities. The images of FIG. 2 are formed from segmentation of parenchyma, vasculature, and lesions.

The fused anatomical model is used as reference space for subsequent data integration. Act 24 provides for further data integrations, such as generating a liver function map using information from other imaging modalities. Information from one or more of the imaging modalities used to create the anatomy model may contribute function information.

In act 24, a liver function map is estimated. The function of the liver is represented by characteristics of the tissue (e.g., substrate), flow, perfusion, and/or microvasculature. Information not provided by the anatomy model is added or created. In addition to the spatial arrangement of anatomy, information about the function of the liver is provided. The information is added as one or more maps. The maps are models of the functions of the liver, such as labeled voxels representing a measured characteristic of the function.

The map represents a one, two, or three-dimensional distribution of the function. Different functions are represented with the same or different dimensionality (e.g., two dimensions for one function and three dimensions for another). The function map or component maps have the same or different spatial resolution.

The different functions are acquired from different imaging modalities. For example, perfusion and elasticity imaging modes are used to measure corresponding perfusion and substrate characteristics of the liver. Any number of different imaging modalities and corresponding functions may be added. One or more function maps or models may be based on a combination of information from maps or models used for the anatomy and/or other functions.

The anatomy model is enhanced with a quantitative, multi-modality liver function map. For example, a detailed multi-modality liver function map is calculated and provides a comprehensive assessment of liver function through anatomy, substrate and perfusion quantification.

Acts 26, 28, and 30 are three example function maps that may be combined to provide the comprehensive liver function map. Additional, different, and/or fewer function maps may be used.

The maps for the different functions are aligned, such as using any of the alignment or registration discussed above for the anatomy model. Each map may be aligned to the anatomy model. Alternatively, the function maps are spatially aligned with each other, and then the liver function map based on the combination of component maps is aligned with the anatomy model. A machine-learnt or image processing-based fusion of any function map with the anatomy model may be used to align and/or to generate a model incorporating both anatomy and function.

In act 26, a substrate model is generated. A map of the tissue constituent or viscoelastic properties is generated. For example, a map of the stiffness of the tissues in the liver of the patient is formed. The stiffness, viscosity, other viscoelastic property, or combinations thereof is estimated.

The substrate map is generated from scan data of one or more modalities. For example, a scan is performed in an elasticity imaging mode. The map of liver stiffness and/or viscosity is generated non-invasively. Direct elastography measurements (e.g. ultrasound elastography and/or MR elastography) are used with or without further filtering. Shear-wave imaging may be used to estimate stiffness and viscosity. A shear-wave is generated using acoustic radiation force impulse (ARFI) or another stressor (e.g., native breathing or cardiac motion), and a shear-wave speed is measured. From that map, an inverse shear-wave propagation model combining elasticity and viscosity may used to estimate parameters locally. Alternatively, the shear wave speed is used as the measure of the substrate as the speed varies based on the viscoelastic properties of the liver tissue.

In other embodiments, the stiffness and/or viscosity are estimated indirectly. Motion of the liver is detected, such as with ultrasound scanning. Motion due to shear-waves is acquired to evaluate the mechanical properties of an organ of a patient. Given the liver motion visible in the images, liver stiffness is estimated by solving an inverse biomechanical model (i.e., inverse modeling). Shear-wave propagation in the tissue is simulated based on shear modulus and viscosity values for the tissue using a computational model of shear-wave propagation. The simulated shear-wave propagation is compared to observed shear-wave propagation in the shear-wave images of the tissue using a cost function. Patient-specific shear modulus and viscosity values for the tissue are estimated to optimize the cost function comparing the simulated shear-wave propagation to the observed shear-wave propagation. Other estimations of the substrate map may be used.

The resulting substrate map or maps are aligned to the anatomical model using image fusion. Any of the alignment or registration approaches discussed above for the different modalities used in the anatomy model may be used. In one embodiment, $B_0$ MR images are used to align MR elastography measurements with the MR measurements used in the anatomy model. In the case of ultrasound-based elastography, sensor-based fusion is employed to automatically align the ultrasound imaging to the available MR scan data of the anatomy model. The position of the transducer used in ultrasound scanning is determined relative to the coordinate system of the MR scan data or a world/room coordinate system calibrated to the MR coordinate system. Scan data registration may alternatively be used.

Figure 3:
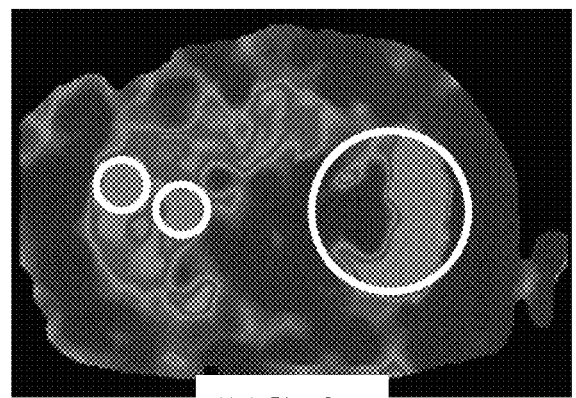
FIG. 3 shows an image of a substrate model.

FIG. 3 shows an example substrate map as a MR liver elastography map estimated from liver motion due to respiration. The small circles are not provided on the map but are included in FIG. 3 to show two stiff nodules in the liver. The large circle is also not provided on the map, but is included in FIG. 3 to show the spine and corresponding relatively high stiffness as compared to the soft tissue of the liver. Any regions of increased stiffness are shown. In alternative embodiments, any annotation or highlighting (e.g., circles) added by image processing or user input may be included in the substrate map.

In act 28, a perfusion model is generated. The perfusion model is a map of fluid perfusion of the soft tissue of the liver of the patient. The level of perfusion or flow not necessary represented in the anatomy model into tissue of the liver is quantified. Areas of hypo and/or hyper intense perfusion (i.e., areas of varying perfusion as perfusion is homogeneous in healthy livers) may be identified.

The perfusion map is generated by measuring perfusion of the liver with a perfusion imaging modality. Any quantitative perfusion imaging may be used. For example, contrast agent-based ultrasound perfusion imaging is used. MR, CT, or angiogram imaging of perfusion may be used.

The perfusion measurements are used as the perfusion model. Specific regions may alternatively or additionally be used as or in the perfusion model. For example, thresholding is applied to locate tumor and/or vessel regions. The anatomy model may be used to distinguish tumor and vessel regions of hyper-intense or higher perfusion. Hyper-intense areas related to vessels or overlap of vessels are located. Any hyper-intense area related to hyper-vascularized tumors are located. Hypo-intense areas, if within the parenchyma, are located as an area of impaired liver function that can be safely resected.

As an alternative to thresholding, hyper and hypo-perfusion may be quantified based on a difference between the measured perfusion for the patient and an atlas or template perfusion map. A perfusion map across a population of healthy subjects is generated. This reference perfusion model is created by first bringing all the perfusion images of the healthy subjects into one coordinate system and creating a reference liver atlas by combination (e.g., average perfusion with or without standard deviation per voxel). The reference perfusion map may be transported into the atlas space and voxel-wise statistics incorporated. The measured perfusion for the specific patient is then compared to this "normal" or reference model. Threshold-based criterion may be employed to identify abnormalities (e.g. deviation of measured perfusion of the patient beyond two standard deviations of the mean in the atlas). In another alternative, deep-learning or other machine-learnt classification is used to automatically locate the regions of abnormal perfusion based on input of the measured patient perfusion with or without input of other information (e.g., anatomy model).

Figure 4:
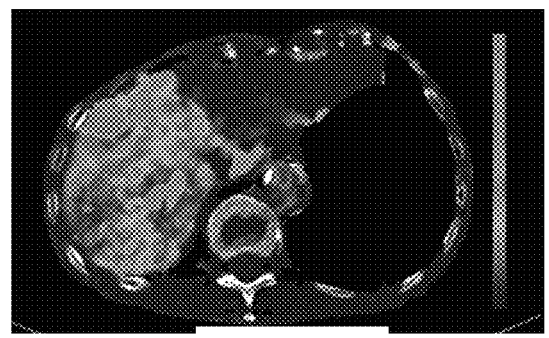
FIG. 4 shows an image of a perfusion model.

FIG. 4 shows an example liver perfusion map of a cross-section of the liver. The liver perfusion map is generated by CT with hepatic arteriography of hepatocellular carcinoma.

In act 30, a microvascular model of the liver of the patient is inferred. Tumor microvasculature plays a role in tumor growth and evolution. Having a good understanding of the microvasculature may further help characterize tumor aggressiveness and assess embolization and drug delivery strategies. Unfortunately, imaging the microvasculature is still a challenge. The microvascular vessels may not be distinguishable from medical scan data such that segmentation may be performed without more. In another embodiment, imaging modalities that are able to visualize and quantify micro-vasculature (e.g. high-framerate, high-resolution Doppler ultrasound) may be integrated directly.

The microvascular map is inferred from other component maps (e.g., substrate and perfusion) of the multi-modality liver function map, an image of flow, flow derived from the anatomy model, and/or the anatomy model. The inference is an indirect coupling of the microvascular map with a computational model of angiogenesis. The microvascular map is an inverse solution inferred from angiogenesis modeling.

In one embodiment, a fractal model is used to create the microvasculature tree between the visible vessels and the tumors. Sub-branches are created at a rate per distance and/or a number based, at least in part, on the amount of perfusion for the location or locations. The sub-branches are created from the vessels of the anatomy model to the tumor of the anatomy model. Vessels and tumor shapes are obtained from the flow and/or anatomy model. The substrate map may be used for fractal branching, such as the rate and/or number being based on stiffness (i.e., composition of the extra-cellular matrix). Stiff tissue may have less microvasculature. The fractal model is controlled by tumor angiogenesis factors of the tumor (e.g., deriving amount blood supply of the tumor from the anatomy model and/or image of flow). Stiffness and anisotropy of the extra-cellular matrix are estimated from the perfusion and substrate map. The parameters of the angiogenesis model around the tumor or lesion are estimated to match the measured local perfusion. If available, biomarkers that characterize fibrosis and angiogenesis are used to further refine the microvascular model parameters. Other microvascular modeling may be used, such as a template of microvascular fit to tumor size, shape, blood supply, perfusion, substrate, flow, and/or other information.

For act 24, the liver function map is the collection of component maps. The component maps may be transformed to a common coordinate system or remain in the native coordinate systems. The component maps may be combined, such as labeling each voxel of the common liver function map with information from the various component maps. In another embodiment, the combination uses regressors or other machine-learnt classifier. Given clinical end-points in training, the machine-learnt classifier determines voxel, structure, or organ function based on the input component information. The liver function map summarizes spatial variations of liver function. Structure or organ-wise mapping may alternatively be used, such as providing one or more liver function values for each structure or the entire liver.

The liver function map may indicate areas with low function that may be safely resected or be used to assess an extent of a remnant of liver after resection. Any of the component information may be used for assessment, such as applying thresholds to each type of information independently or applying a combination of thresholds. Any image processing or machine-learnt classification may be used to assess. If available, blood or tissue biomarkers are employed to refine the assessment of liver disease stage.

In act 32, a computational model of physiology of the liver is estimated. To model change to the liver, the computational model is formed. The computational model is generative for in-silico therapy evaluation and optimization. Changes to the liver may be modeled with the corresponding changes in other parts or characteristics of the liver. The computational model is a physics, biomechanical, chemical, and/or other model incorporating material properties of the liver. The computational model may be run on a local computer, on the cloud (e.g., a server) through web-services. Several therapy options may be tested interactively, or fully automatically, with the generation of a report with recommended options (e.g., the best one or the top N therapy options measured with any criterion or criteria)

To personalize the generative model, the anatomy model, liver function model, one or more component function models (e.g., perfusion, substrate, and/or microvascular), and/or other information may be incorporated. The generative model may use finite element method, wavelets, or other representation interrelating various characteristics. In one embodiment, the generative model is fit to the particular patient based on the liver function map, anatomy model, and biomarkers.

The generative liver model includes biomechanics, hemodynamics, metabolism, cellular viability, and/or heat diffusion. Additional, different, or fewer components of the computational model of the liver may be used. While the liver function map represents the measured and/or modeled function, the computational map represents the physics and/or chemistry of the liver at one or more scales (e.g., cellular, micro, and/or organ).

For hemodynamics, computational fluid dynamics (CFD) is used to estimate blood flow through the hepatic vessels and within the parenchyma. A combined CFD-porous solver based on the Lattice-Boltzmann method (LBM) calculates the blood flow throughout the entire liver domain given a porosity map. The porosity map represents the fluid porousness of the liver and is inversely solved using the perfusion map, inflow profile, and/or outflow pressure. The porosity map is also controlled by the inflow profiles for major arteries. The anatomy model or flow map (e.g., measured with MR) may be used to determine the inflow to a tumor or the liver. The anatomy model or flow map may be used to infer the outflow pressure. Alternatively, the outflow pressure is measured invasively or inferred from cuff pressure.

For biomechanics, a visco-poro-hyper-elastic model is used to calculate liver parenchyma deformation. The model represents the viscosity, porosity, and elasticity of the liver. The model is coupled with a surface membrane to simulate Glisson's capsule and tubular models of vessels to increase the realism of the calculated deformations. Each component (i.e., viscosity, porosity, and elasticity) is linked through hard constraints. Any constraint limiting the relationships between the components may be used. The surface membrane may constrain deformation transfer into an interior of the liver. The Newton equation of dynamics is solved using finite element models to fit the visco-poro-hyper-elastic model for the patient. The biomechanical model is personalized using the elastograms and the perfusion maps.

For metabolism and/or cellular viability, the liver metabolism (galactose, iron, and/or nutrients) are included in the generative model. Metabolic cellular models have been developed and multi-scale (e.g., cellular and organ) techniques applied to scale these cellular models at the organ level. One or more metabolism models are used when known metabolic dysfunctions are present in the patient, such as identified through blood biomarkers. Metabolism and cellular viability models are described through chemical equations (e.g., cellular growth model based on nutrient level) that are solved at each voxel of the CFD-LBM grid. The model is controlled by the level of oxygen transported by the blood flow from perfusion maps and other parameters tuned using blood biomarkers. Similarly, cellular viability is modeled as a response to heat level. The cellular viability may be calculated given heat, allowing capture of the ablation process during thermal therapy.

For bioheat diffusion, the bioheat model is any soft tissue or biological heat diffusion model. The bioheat model is used to calculate heat diffusion in the case of thermal ablation (e.g., radio frequency ablation, micro-wave, cryotherapy, or acoustic ablation).

The generative model is formed as a combination of the various components. Each component may be independent.

Each of the components may be activated or deactivated depending on the disease under consideration for the patient.

In act 34, the generative model and/or liver function model is used to recommend a next step in a clinical workflow. Any of the components of the generative model and/or the liver function model (e.g., the substrate model, the perfusion model, and/or the microvascular model) may be used. Other information, such as blood biomarker information, may be included. Once all the information is integrated, precise recommendations may be obtained automatically on the next steps of the clinical workflow. The clinical workflow links measured features of the liver to specific actions.

Based on thresholding, imaging processing, machine-learnt classification, analysis by multi-variate analysis, logic flow, and/or other analysis, the next step is determined. A guideline, decision support system, or machine-learnt clinical action is used to select a next step for the patient. For example, the current state of the patient represented in the liver function map is compared to one or more guidelines. The guidelines relate abnormalities to clinical actions. Thresholds or other indications of abnormalities may be included, allowing for recommendation based on the liver function map. In another example, a multi-variate analysis of the generative model provides discriminative features for decision support. Because the computational model is generative, different physiological conditions (e.g. increased portal pressure or drug application) are tested to assess liver function and predict potential failure. The results from the multi-variate analysis may be used to recommend one step over another, such as to maximize liver function while minimizing patient risk.

In act 36, a therapy outcome is calculated. For a recommended therapy, once a therapy is decided upon by a physician, and/or as part of planning to select a therapy, a predicted outcome of the therapy is calculated. The generative model and/or liver function map are used to determine therapy outcome before the therapy is performed on the patient. The therapy planning is for ablation, surgery (e.g., resection), chemo- or radio-embolization, drug therapy, and/ or other therapy. Each of these therapies affect the liver function in one or more ways. For instance, after surgery, the perfusion is affected and the modeling is used to determine if the perfusion of the remaining tissue is still acceptable. As another example, chemo- and radio-embolization directly affect the tumor region and surrounding tissue, including microvasculature. The therapy outcome predicts how much of the liver and/or other organs are affected.

Acts 38 and 40 represent on example of calculating the therapy outcome. A feedback from the generative model to update one or more component maps of the liver function model allows the function of the liver in response to therapy to be assessed. The change from the generative model is used to update the function information for determining the outcome. For example, the perfusion map is updated to account for ablation effects or liver surgery. As another example, the anatomy model is updated to show a region of ablation or liver resection based on the generative model change. In other embodiments, the outcome is calculated from the generative model or without update of the liver function map. For example, a machine-learnt classifier indicates an outcome in response to input of the change from the generative model and the liver function map. The classifier is trained using paired clinical data (e.g., images, lab test, and liver function map) and outcome.

In act 38, a change in the liver due to therapy is modeled with the computational model. The application of the therapy to the liver is simulated using the generative model. The generative model may be used to determine one or more effects on the liver of the therapy. The generative model is queried to test one or more therapy strategies. The generative model provides characteristics of the liver that are changed due to the therapy. The heat, removal, or other alteration due to therapy is incorporated into the generative model, which outputs a resulting change to the rest of the liver.

In act 40, the liver function map is updated. The change to the liver due to therapy is used to update one or more component maps of the liver function map. In response to the modeled change in the liver, the anatomy model, the substrate model, the perfusion model, the microvascular model, or combinations thereof are updated. The update reflects the results of the therapy. The resulting function of the liver after therapy is provided based on the feedback from the computational model.

Any update may be used. For example, the mesh for one or more structures in the anatomy model is varied. As another example, the perfusion is increased or decreased for locations based on cellular viability, biomechanics, and/or hemodynamics. In another example, the substrate map is altered to account for different cellular matrix due to cellular viability, metabolism, hemodynamics, or biomechanics.

The update uses an inverse solution. Given the changes or resulting computational model due to the change, the variation or modeled state of the function is determined. In other embodiments, the update is provided by logic or machine-learnt knowledge of an alteration in function given the information from the generative model. Alternatively, a scan is simulated from the generative model. The scan simulates the detection process for the given mode of imaging. The function map is updated by being replaced with the simulated function map.

In one example, the liver perfusion map is updated given a resection pattern to assess risks of liver failure. The metabolism from the generative model provides an indication of where and by how much the perfusion changes. The function of the tissue remaining after resection is determined.

In another example, combined therapy is modeled. The perfusion map is linked with ablation. The generative map determines a change due to ablation and surgery, such as determining a change in biomechanics and hemodynamics based on cellular viability, metabolism, and bioheat resulting from ablation and surgery. This change is linked to the perfusion. The hemodynamics indicates an amount of change in perfusion for each location, and the perfusion map is updated based on the amount of change by location. The effect of embolization as a change due to therapy may be used to update the perfusion.

In another example, for drug delivery therapy, the CFD for the hemodynamic component of the generative model is used to calculate molecule transport due to the drug. When combined with the model of microvasculature, the locations of transport (e.g., how far the drug will go and how much is lost in other vessels) is determined as an outcome. Combined with pharmacokinetic models, the effect of the drug on the tumor may be calculated and the liver model updated accordingly (changes in tumor size, vascularization, etc.)

Other changes and feedback may be provided. For example, changes in biomarkers are determined to assess systemic effects (e.g., decrease in liver fibrosis markers as an indicator of preserving cardiac function).

The update to the function is based on modeling. The generative model is linked to the function map or component maps so that a change output by the generative model results in a change in the function. In another embodiment, a machine-learnt classifier predicts the change in function in response to input of the change or data generated by the computational model.

In act 42, the therapy outcome is output. An image indicating the therapy outcome is provided. Other outputs may be used, such as transfer over a network, storage in memory, or addition to a computerized medical record for the patient.

The image includes an alphanumeric, graphical, or spatial representation of the outcome. For example, the image shows a spatial distribution of liver function from one or more updated function maps. The function may be overlaid on an image of the anatomy of the liver. In another example, a measure of function (e.g., liver failure) is added as an annotation over an image of the anatomy and/or function. Any of the component maps, anatomy model, and/or spatial distribution from the generative model may be represented in the image.

The image may be a cross-section through the liver. Alternatively, the image is a rendering of the three-dimensional distribution to a two-dimensional display, 3D holographic display, an augmented reality display, or virtual reality display. The scan data may be used to generate an image of the liver instead of or in addition to the anatomy model. In other embodiments, the image provides information without a spatial representation of the liver, such as indicating liver failure prediction in a report.

Figure 5:
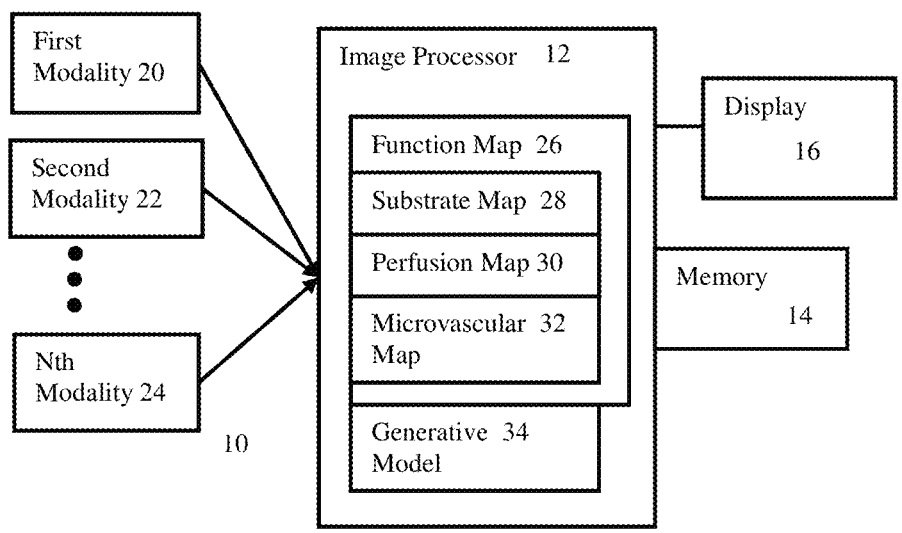
FIG. 5 is a block diagram of one embodiment of a system for liver modeling from medical scan data.

FIG. 5 shows a system 10 for liver disease characterization and therapy planning. The system implements the method of FIG. 1 or another method. A functional map 26 and generative model 34 are personalized to a liver of a patent based on scan data from multiple medical imaging modalities 20, 22, 24. The functional map 26 and generative model 34 are used to recommend clinical action for the patient, to characterize a state of the liver or lesions in the liver, and/or to plan for therapy. For therapy planning, change in the liver is modeled by the generative model 34 and the resulting function map 26 is updated based on the change to characterize the functional results of the proposed therapy.

The system includes an image processor 12, a memory 14, a display 16, and multiple imaging modalities 20, 22, 24. The image processor 12, memory 14, and display 16 are shown separate from the imaging modalities 20, 22, 24, such as being part of a workstation, computer, or server. In alternative embodiments, the image processor 12, memory 14, and/or display 16 are part of one or more of the imaging modalities 20, 22, 24. In yet other embodiments, the system 10 does not include the imaging modalities 20, 22, 24. Additional, different, or fewer components may be used.

Any number of modalities 22, 22, 24 may be provided. The modalities 20, 22, 24 are the same or different types of scanners. CT, MR, ultrasound, PET, SPECT, camera, or other scanners may be used. The modalities 20, 22, 24 may be from a fewer number of types of scanners, but used to measure different characteristics. In one embodiment, the modalities 20, 22, 24 include MR, CT, and ultrasound scanners. Further modalities 20, 22, 24 are provided by using one or more of these types of scanners for different measurements, such as using MR for flow, anatomy, and perfusion.

The scans by the modalities 20, 22, 24 provide the scan data representing the liver. Any of the types of scan data used for the modeling may be provided, such as elasticity, perfusion, anatomy, and/or flow scan data.

The memory 14 is a buffer, cache, RAM, removable media, hard drive, magnetic, optical, database, or other now known or later developed memory. The memory 14 is a single device or group of two or more devices. The memory 14 is shown associated with or part of the image processor 12, but may be outside or remote from other components of the system 10. For example, the memory 14 is a PACS database storing the scan data from the modalities 20, 22, 24.

The memory 14 stores the scan data, models, maps, and/or information used in image processing, creating the function map, creating the generative model, calculating from the generative model, updating the function map, or other processing. Any format may be used, such as voxels interpolated to a three-dimensional grid or data representing parallel or non-parallel planes.

The memory 14 is additionally or alternatively a non-transitory computer readable storage medium with processing instructions. The memory 14 stores data representing instructions executable by the programmed image processor 12. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The image processor 12 is a general processor, digital signal processor, three-dimensional data processor, graphics processing unit, application specific integrated circuit, field programmable gate array, digital circuit, analog circuit, quantum computers, combinations thereof, or other now known or later developed device for modeling the liver from scan data with or without blood biomarkers or clinical data. The image processor 12 is a single device, a plurality of devices, or a network. For more than one device, parallel or sequential division of processing may be used. Different devices making up the image processor 12 may perform different functions, such as an automated anatomy detector and a separate device for forming the function map 26 and generative model 34. In one embodiment, the image processor 12 is a control processor or other processor of a medical diagnostic imaging system, such as a CT or MR image processor. The image processor 12 is a hardware device configured by or operating pursuant to stored instructions, design (e.g., application specific integrated circuit), or hardware to perform various acts described herein.

The image processor 12 is configured to create an anatomical model by segmenting with scan data from one or more of the modalities 20, 22, 24. The liver function map 26 is created by extracting or acquiring scan data representing the component functions, such as a substrate map 28 from elasticity imaging and a perfusion map 30 from perfusion imaging. The microvascular map 32 is inferred using modeling, such as fractal or other modeling of microvascular vessels around a tumor being inversely solved based on the measured perfusion in the region, blood flow in the region, and/or pressure. The image processor 12 is configured to fit a generative model 34 with any number of components to the scan data, blood biomarkers, and/or the function map 26. The image processor 12 may model therapy using the generative model 34, update the function map 26, and/or output a recommendation or expected outcome from therapy.

The image processor 12 may generate an image. The generative model, scan data, anatomical model, and/or function map is used to generate an image. The recommendation and/or therapy results may be output as the image, as part of the image, or an annotation on an image. The image provides a visualization of the liver, recommendation, and/or therapy outcome (e.g., function map updated to account for possible therapy).

The display 16 is a CRT, LCD, plasma, projector, printer, or other output device for showing an image or other output of the image processor 12 and/or modalities 20, 22, 24. The display 16 displays an image of the detected anatomy, detected function, updated anatomy, and/or updated function for a proposed therapy.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for liver modeling from medical scan data, the method comprising:
   generating an anatomy model of structures of a liver of a patient from scan data of at least a first imaging system of corresponding first imaging modality;
   generating a substrate model of stiffness of the liver of the patient from scan data of a second imaging modality different than the first imaging modality;
   generating a perfusion model of fluid perfusion of the liver of the patient from scan data of a third imaging modality different than the first and second imaging modalities;
   inferring a microvascular model of the liver of the patient from the anatomy model, substrate model, and perfusion model;
   estimating a computational model of physiology of the liver from the substrate model, perfusion model, anatomy model, and the microvascular model;
   modeling a change in the liver due to therapy with the computational model;
   updating, in response to the modeling of the change, the anatomy model, the substrate model, the perfusion model, the microvascular model, or combinations thereof; and
   outputting an image representing function of the liver based on the updated anatomy model, the substrate model, the perfusion model, the microvascular model, or combinations thereof.

2. The method of claim 1 wherein generating the anatomy model comprises generating the anatomy model from magnetic resonance as the first imaging modality and computed tomography as a fourth imaging modality, different ones of the structures being from different ones of the first and fourth imaging modalities.

3. The method of claim 1 wherein generating the anatomy model comprises generating the anatomy model of soft tissue, vasculature, biliary system, and lesions as the structures.

4. The method of claim 1 wherein generating the substrate model comprise generating the substrate model from elasticity imaging as the second imaging modality.

5. The method of claim 1 wherein generating the substrate model comprises generating the substrate model from direct measurement of the stiffness or inverse modeling.

6. The method of claim 1 wherein generating the perfusion model comprises measuring perfusion with perfusion imaging as the third imaging modality.

7. The method of claim 1 wherein inferring the microvascular model comprises inferring from inverse angiogenesis modeling.

8. The method of claim 1 wherein estimating the computational model comprises estimating biomechanics, vessel hemodynamics, and metabolism.

9. The method of claim 8 wherein estimating the computational model comprises estimating bio-heat diffusion and cellular viability.

10. The method of claim 1 further comprising recommending a next step in a clinical workflow based on the computational model, the anatomy model, the substrate model, the perfusion model, the microvascular model, or combinations thereof.

11. The method of claim 1 wherein modeling the change comprises modeling therapy applied to the liver with the computational model, and wherein updating comprises updating to reflect results of the therapy.

12. The method of claim 1 wherein updating comprises updating with feedback from the computational model.

13. The method of claim 1 wherein outputting comprises outputting the image with an indication of liver failure.

* * * * *